United States Patent [19]
Ward et al.

[11] Patent Number: 5,978,702
[45] Date of Patent: *Nov. 2, 1999

[54] TECHNIQUES OF TREATING EPILEPSY BY BRAIN STIMULATION AND DRUG INFUSION

[75] Inventors: Scott R. Ward, Inver Grove Heights; Mark T. Rise, Monticello, both of Minn.

[73] Assignee: Medtronic, Inc., Minneapolis, Minn.

[*] Notice: This patent is subject to a terminal disclaimer.

[21] Appl. No.: 08/957,239

[22] Filed: Oct. 24, 1997

Related U.S. Application Data

[63] Continuation of application No. 08/647,590, May 13, 1996, Pat. No. 5,713,923.

[51] Int. Cl.$^6$ ........................................ A61N 1/00
[52] U.S. Cl. .................. 607/3; 604/50; 604/67; 604/891.1
[58] Field of Search .............................. 607/1–3, 45, 116, 607/120, 62; 604/891.1, 65–67, 50

[56] References Cited

U.S. PATENT DOCUMENTS

| | | |
|---|---|---|
| 3,993,046 | 11/1976 | Fernandez et al. . |
| 4,692,147 | 9/1987 | Duggan . |
| 4,702,254 | 10/1987 | Zabara . |
| 4,867,164 | 9/1989 | Zabara . |
| 5,025,807 | 6/1991 | Zabara . |
| 5,031,618 | 7/1991 | Mullett . |
| 5,154,172 | 10/1992 | Terry, Jr. et al. . |
| 5,269,303 | 12/1993 | Wernicke et al. . |
| 5,293,879 | 3/1994 | Vonk et al. . |
| 5,299,569 | 4/1994 | Wernicke et al. . |
| 5,474,547 | 12/1995 | Aebischer et al. ................... 604/891.1 |
| 5,522,863 | 6/1996 | Spano et al. . |
| 5,540,734 | 7/1996 | Zabara . |
| 5,676,655 | 10/1997 | Howard et al. ......................... 604/116 |
| 5,683,422 | 11/1997 | Rise . |
| 5,707,396 | 1/1998 | Benabid . |
| 5,711,316 | 1/1998 | Elsberry et al. ........................... 604/67 |
| 5,713,923 | 2/1998 | Ward et al. ........................... 604/891.1 |
| 5,716,377 | 2/1998 | Rise et al. .................................... 607/2 |
| 5,735,814 | 4/1998 | Elsberry et al. . |
| 5,752,979 | 5/1998 | Benabid . |
| 5,792,186 | 8/1998 | Rise . |
| 5,800,474 | 9/1998 | Benabid et al. . |
| 5,832,932 | 11/1998 | Elsberry et al. . |
| 5,833,709 | 11/1998 | Rise et al. . |

OTHER PUBLICATIONS van Horne et al., "Multichannel Semiconductor–based electrodes for in vivo electrochemical and electrophysical studies in rat CNS", *Neuroscience Letters*, 120, pp. 249–252 (1990).

Benabid et al., "Long–term suppression of tremor by chronic stimulation of the ventral intermediate thalamic nucleus", *The Lancet*, vol. 337, pp. 403–406 (1991).

Benabid et al., "Vim and STN Stimulation in Parkinson's Disease", *Movement Disorders*, vol. 9, Suppl. 1, Abstract M39 (1994).

Limousin et al., "Effect on Parkinsonian signs and symptoms of bilateral subthalamic nucleus stimulation", *The Lancet*, vol. 345, pp. 91–95 (1995).

Bergman et al., "Reversal of Experimental Parkinsonism by Lesions of the Subthalamic Nucleus", *Science*, 249:1436–1438 (1990).

(List continued on next page.)

*Primary Examiner*—William E. Kamm
*Assistant Examiner*—George R. Evanisko
*Attorney, Agent, or Firm*—Banner & Witcoff, Ltd.

[57] ABSTRACT

Techniques using one or more drugs and electrical stimulation for treating a neurological disorder, including epilepsy, by means of an implantable signal generator and electrode and an implantable pump and catheter. A sensor is used to detect a seizure or symptoms resulting from the onset of a seizure. A microprocessor algorithm analyzes the output from the sensor in order to regulate the stimulation and drug dosage delivered to the neural tissue.

23 Claims, 5 Drawing Sheets

OTHER PUBLICATIONS

Depaulis et al., "Endogenous Control of Epilepsy: The Nigral Inhibitory System", *Progress in Neurobiology*, 42:33–52 (1994).

Gale, "Mechanisms of Seizure Control Mediated by Gamma–Aminbutyric Acid: Role of the Substantia Nigra", *Federal Proceedings* vol. 44(8):2414–2424 (1985).

Cooper et al., "The Effect of Chronic Stimulation of Cerebellar Cortex on Epilepsy in Man", *The Cerebellum, Epilepsy Behavior*, Cooper Riklan and Snider ed. Plenum Press, NY. pp. 119–171 (1974).

Velasco et al., "Electrical Stimulation of the Centromedian Thalamic Nucleus in Control of Seizures: Long–Term Studies" *Epilepsia*, 36(1):63–71 (1995).

Sussman et al., "Anterior Thalamic Stimulation in Medically Intractable Epilepsy Part II: Preliminary Clinical Results", *Epilepsia*, 29, No. 5 (1988).

Durand, "Electrical Stimulation Can Inhibit Synchronized Neuronal Activity", *Brain Research*: 382, 139–144 (1986).

Durand et al., "Desynchronization of Epiletiform Activity by Extracellular Current Pulses in Rat Hippocampal Slices", *Journal of Physiology*, 480.3, pp. 527–537 (1994).

Schiff et al., "Controlling Chaos in the Brain", *Nature*, vol. 340, pp. 615–620 (Aug. 25, 1994).

Smith et al., "Rabid Cessation of Focally Induced Generalized Seizures in Rats Through Microfusion of Lidocaine Hydrochloride into the Focus", *Epilepsia*, 34(1):43–53 (1993).

Depaulis et al., "Suprressive Effects of Intranigral Injection of Muscimol in Three Models of Generalized Non–Convulsive Epilepsy Induced by Chemical Agents", *Brain Research*, 498:64–72 (1989).

Mirski et al., "Anterior Thalamus and Substantia Nigra: Two Distinct Structures Mediating Experimental Generalized Seizures", *Brain Research*, 397:377–380 (1986).

Qu et al., "A Seizure Warning System for Long–Term Epilepsy Monitoring", *Neurology* 45:2250–2254 (1995).

Osorio et al., "A Method for Accurate Automated Real–Time Seizure Detection", *Epilepsia*, vol. 36, Supplement 4 (1995).

Crichton, "The Terminal Man", First Ballatine Books Edition (Jan. 1988), pp. 16–27 (Copyright 1972).

Moss, "Chaos Under Control", *Nature*, vol. 370, pp. 596–620, (1994).

Martinez et al., "Toxicology and Kinetics of Long–Term Intraventricular Infusion of Phenytoin and Valproic Acid in Pigs: Experimental Study", *Acta Neurochirurgica*, Suppl. 52, pp. 3–4 (1991).

Durand et al., "Control of Abnormal Electrical Activity with Applied Electrical Fields", *IEEE Engineering in Medicine & Biology Society 10th Annual International Conference*, (1988).

Glanz, "Do Chaos–Control Techniques Offer Hope for Epilepsy," *Science*, vol. 265, p. 1174 (Aug. 26, 1994).

Alexander et al., "Basal Ganglia–thalamocortical Circuits: Parallel Substrates for Motor, Oculomotor, 'Prefrontal' and 'Limbic' Functions", *Progress in Brain Res.* 85:119–146 (1990).

Darder, Gomez, Guerro, Pastor, Gil–Salu, "Intrathecal Antiepiletic Drugs in Experimental Epilepsy" *Sterotact Funct Neurosurg*, (1991) :57:147–155.

TECHNIQUES OF TREATING EPILEPSY BY BRAIN STIMULATION AND DRUG INFUSION

"This is a continuation of application Ser. No. 08/647,590, filed May 13, 1996, now U.S. Pat. No. 5,713,923 for which priority is claimed."

BACKGROUND OF THE INVENTION

1. Field of the Invention

This invention relates to neutral-tissue stimulation and infusion techniques, and more particularly relates to such techniques for treating epilepsy.

2. Description of Related Art

Epileptic seizures are the outward manifestation of excessive and/or hypersynchronous abnormal activity of neurons in the cerebral cortex. Seizures are usually self limiting. Many types of seizures occur. The behavioral features of a seizure reflect function of the portion of the cortex where the hyper activity is occurring. Seizures can be generalized, appearing to involve the entire brain simultaneously. Generalized seizures can result in the loss of conscious awareness only and are then called absence seizures (previously referred to as "petit mal"). Alternatively, the generalized seizure may result in a convulsion with tonic-clonic contractions of the muscles ("grand mall" seizure). Some types of seizures, partial seizures, begin in one part of the brain and remain local. The person may remain conscious throughout the seizure. If the person loses consciousness the seizure is referred to as a complex partial seizure.

Researchers have developed several lines of evidence in studies with animals to demonstrate the existence of a system which can control the propagation and/or the generation of different kinds of seizures. The involvement of the substantia nigra, a particular portion of the brain considered to be part of neural circuitry referred to as the basal ganglia, was first suggested by Gale (*Fed. Proc.* 44, 2414–2424, 1985). Considerable evidence has been generated through research to support this observation and was reviewed by Depaulis, Vergnes and Marescaux (Progress in Neurobiology, 1994, 42: 33–52). Researchers have shown that the inhibition of the substantia nigra will increase the threshold for seizure occurrence in experimental animal models of epilepsy.

Neuroscientists now have a better understanding of the neural connections that make up the basal ganglia. These connections are reviewed by Alexander et. al. (Alexander, Crutcher, and DeLong, "Basal ganglia-thalamocortical circuits: parallel substrates for motor, oculomotor, 'prefrontal' and 'limbic' functions." *Prog. Brain Res.* 85: 119–146.). The substantia nigra receives input from the subthalamic nucleus (STN) which is excitatory and involves glutamate as the neurotransmitter conveying information at the synapse. Bergman et al. have shown that a lesion of the subthalamic nucleus will reduce the inhibitory output of the internal segment of the globus pallidus and substantia nigra reticulata (SN) (H. T. Bergman, T. Wichmann, and M. R. DeLong, 1990, *Science,* 249: 1436–1438). The subthalamic nucleus receives input from the external segment of the globus pallidus (GPe). This input is inhibitory using GABA as a transmitter substance. Hence, increased activity of the neurons in GPe will increase inhibition of neurons in the subthalamic nucleus which will reduce the excitation of neurons in the substantia nigra.

Neurosurgeons have been able to diminish the symptoms of many neural disorders by lesioning certain brain areas. Lesions of the ventral lateral portion of the internal Globus Pallidus and Vim Thalamus can alleviate certain disorders of movement. In addition, it has been demonstrated that open-loop Deep Brain Stimulation (DBS) at high frequencies (100 Hz. or higher) of certain brain structures can alleviate, diminish, or completely stop symptoms of tremor, rigidity, akinesia or hemiballism much like creating a lesion. Published targets of stimulation include the VIM (ventral intermediate thalamus), subthalamic nucleus, and internal globus pallidus.

Benabid et al. (*The Lancet,* Vol 337: Feb. 16, 1991, pp 403–406) have shown that stimulation of the Vim nucleus of the Thalamus will block tremor. In this instance, stimulation at frequencies around 100 to 185 pulses per second accomplishes the same physiological response as a lesion of this region. Benabid's research team has extended this work to stimulation of the subthalamus in order to help reduce symptoms of motion disorders ("Vim and STN Stimulation in Parkinson's disease", *Movement Disorders,* Vol 9, Supplement 1(1994); "Effect on Parkinsonian signs and symptoms of bilateral subthalamic nucleus stimulation", *The Lancet,* Vol 345, Jan. 14, 1995.) It has been known for some time that electrical stimulation of neurons at lower stimulus pulse frequencies will activate the neurons.

Electrical stimulation of the nervous system has been used to suppress seizures. Cooper et. al. have stimulated the cerebellum ["The Effect of Chronic Stimulation of Cerebellar Cortex on Epilepsy in Man", I. S. Cooper, I. Amin, S. Gilman an J. M. Waltz in The Cerebellum, Epilepsy and Behavior, Cooper Riklan and Snider ed. Plenum Press, NY, 1974] Velasco et. al. have stimulated Centre Median nucleus of the thalamus [Electrical Stimulation of the Centromedian Thalamic Nucleus in control of Seizures: Long-Term Studies, F. Velasco, M. Velasco, AL Velasco, F Jimenez, I Marquez, and M. Rise, *Epilepsia,* 36(1): 63–71, 1995] Sussman et. al. have stimulated the anterior nucleus of the thalamus to treat epilepsy [Sussman N M, Goldman H W, Jackel R A, "Anterior Thalamic Stimulation in Medically Intractable Epilepsy Part II: Preliminary Clinical Results", *Epilepsia* 1988; 29: 677]. Durand electrically stimulated the focus of seizure origin to inhibit synchronized neuronal activity in the hippocampal slice model [Durand, D. "Electrical Stimulation Can Inhibit Synchronized Neuronal Activity", *Brain Research:* 382: 139–144, 1986., Durand, D. and Warman E., Desynchronization of Epileptiform Activity by Extracellular Current Pulses in Rat hippocampal Slices, *Journal of Physiology* (1994), 480.3] More recently Schiff et. al. used chaos theory to apply stimulation to a seizure focus to abort the seizure[ S. Schiff, K. Jerger, D Duong, T. Chang, M. Spano & W Ditto, "Controlling Chaos in the Brain", *Nature,* Vol 370, Aug. 25, 1994].

Infusion of certain drugs into a region of the brain can affect the excitability of the neurons at the site of infusion. Smith et. al. infused lidocaine hydrochloride into the focus of rats with focally induced generalized seizures showing the seizure could be suppressed [Douglas Smith, Scott Krahl, Ronald Browning and Edwin Barea, "Rapid Cessation of Focally Induced Generalized Seizures in Rats Through Microinfusion of Lidocaine Hydrochloride into the Focus", *Epilepsia,* 34(1):43–53, 1993] Depaulis et. al. [*Brain Research,* 498 (1989) 64–72] have infused muscimol into the substantia nigra of rats suppressing the occurrence of spike-and-wave discharges in animal models of non-convulsive epilepsy. Mirski, McKeon, and Ferrendelli [*Brain Research,* 397 (1986) 377–380] showed that infusion of an inhibitor of GABA transaminase into the anterior thalamic nucleus protected rats against PTZ induced generalized seizures but not those caused by maximal electroshock while infusion of the agent into the substantia nigra had the opposite effect.

Researchers have devised algorithms to detect the onset of a seizure. Qu and Gotman report a system that recognizes patterns of electrical activity similar to a template developed from recording an actual seizure. [H. Qu and J. Gotman, "A Seizure Warning System for Long-term Epilepsy Monitoring", *Neurology*, 1995; 45: 2250–2254.] Osario et. al. have reported an algorithm applied to signals recorded from intracranial electrodes capable of 100% seizure detection rate with 0% false negatives and minimal false positives. [I. Osario, M. Frei, D. Lerner, S. Wilkinson, "A Method for Accurate Automated Real-time Seizure Detection", *Epilepsia*, Vol. 36, Suppl. 4, 1995].

SUMMARY OF THE INVENTION

A preferred form of the invention uses one or more drugs and electrical stimulation to treat a neurological disorder, such as epilepsy. The treatment is carried out by an implantable pump and a catheter having a proximal end coupled to the pump and having a discharge portion for infusing therapeutic dosages of the one or more drugs into a predetermined infusion site in a brain. The treatment also may be carried out by an implantable signal generator and one or more implantable electrodes for electrically stimulating a predetermined stimulation site in the brain.

By using the foregoing techniques, neurological disorders, including epilepsy, can be treated and seizures can be alleviated or prevented with a degree of efficacy and reliability unavailable in prior techniques.

Another form of the invention uses a sensor in combination with the signal generator, one or more stimulating electrodes, pump and catheter to treat a neurological disorder. In this form of the invention, the sensor generates a sensor signal related to a condition resulting from the onset of a seizure, including a seizure itself Control means responsive to the sensor signal regulate the signal generator and pump so that the neurological disorder is treated, and seizures are alleviated or prevented.

By using the foregoing techniques, the symptoms of many neurological disorders, including epilepsy, can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
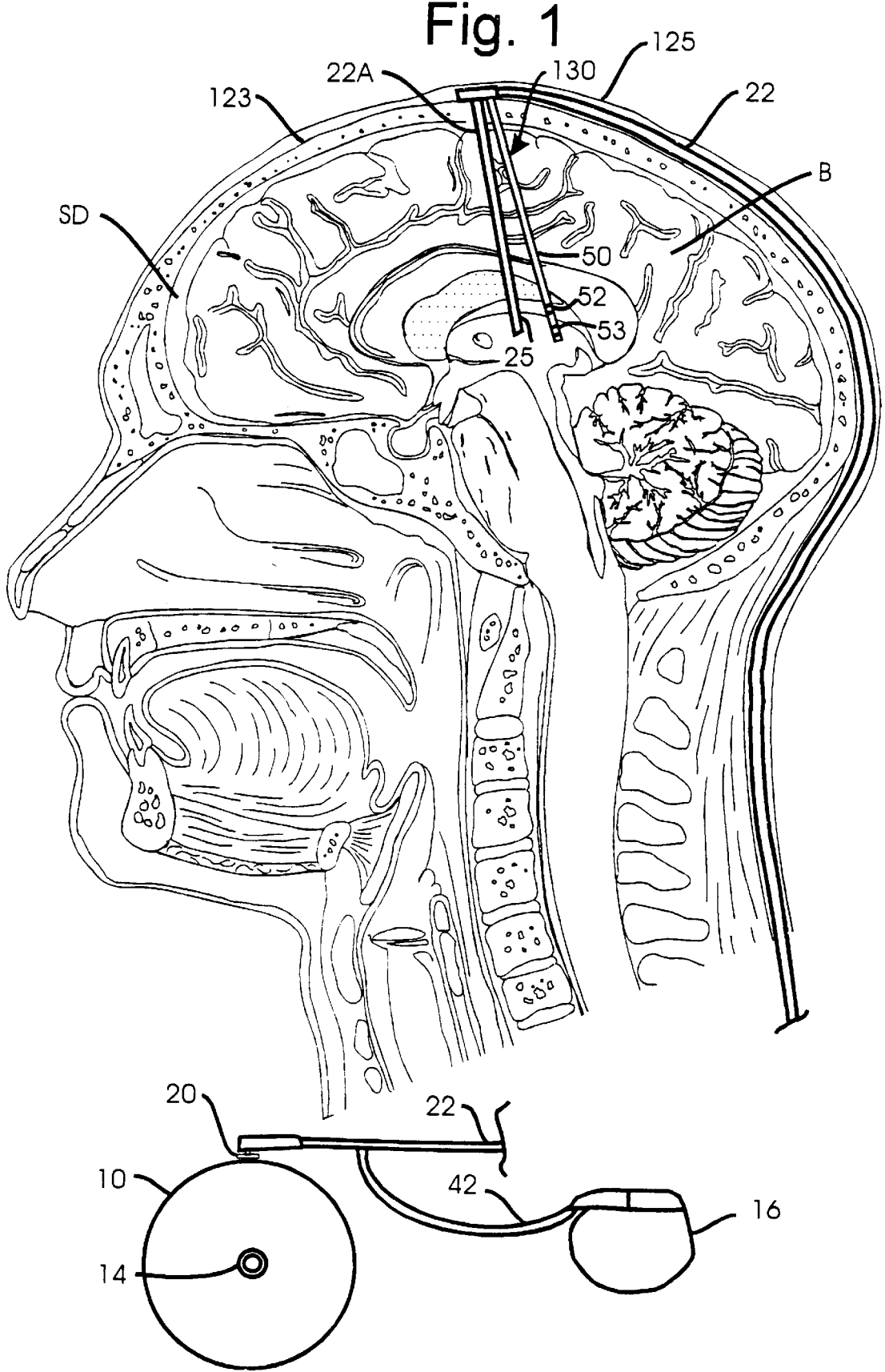
FIG. 1 is a diagrammatic illustration of a combined catheter and electrode implanted in a brain according to a preferred embodiment of the present invention, and a signal generator and pump coupled to the combined catheter and electrode.

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., which is incorporated by reference.

Figure 6:
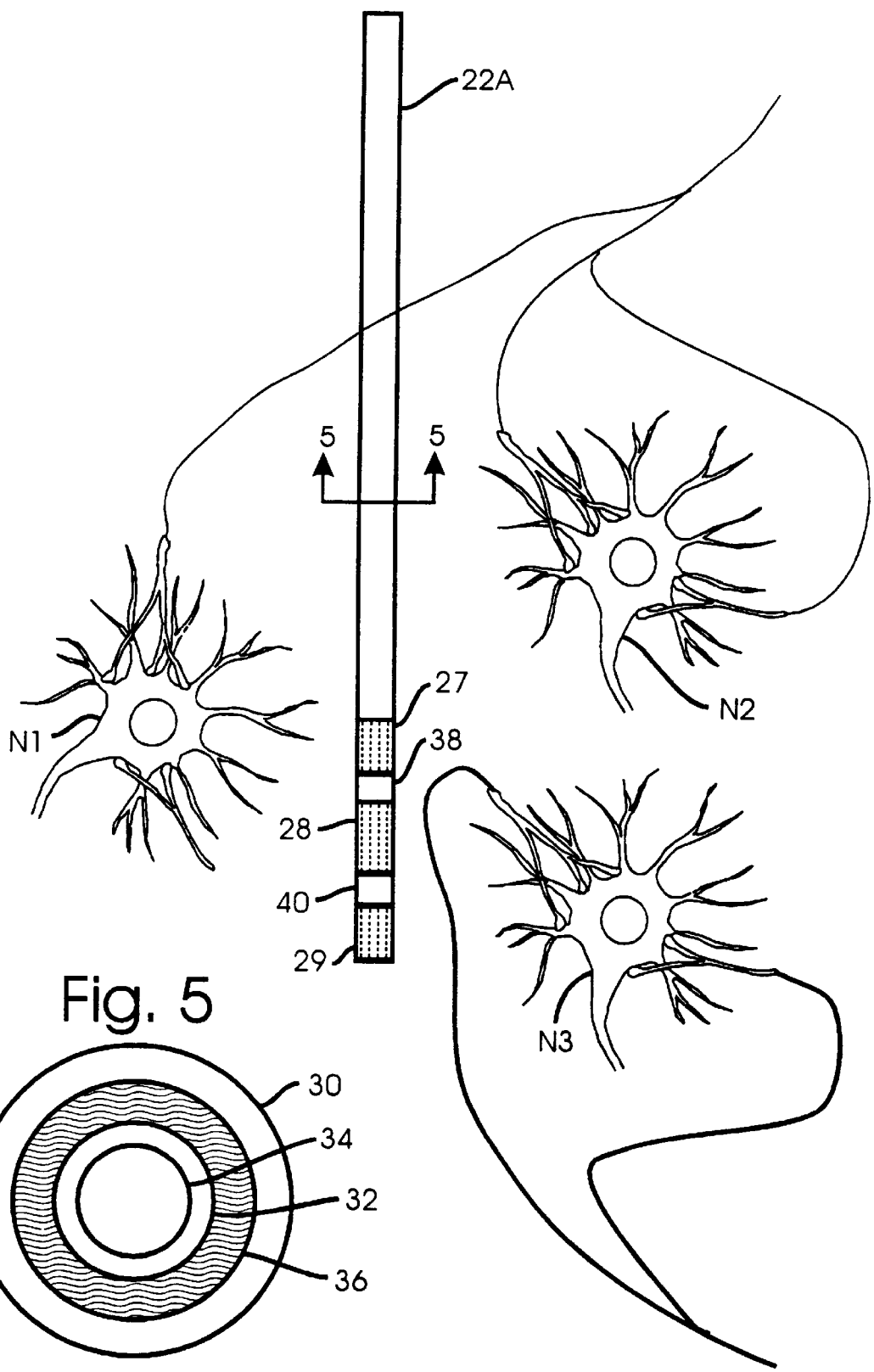
FIG. 6 is a diagrammatical view of the catheter-electrode shown in FIG. 1 arranged adjacent neural tissue.
Figure 5:
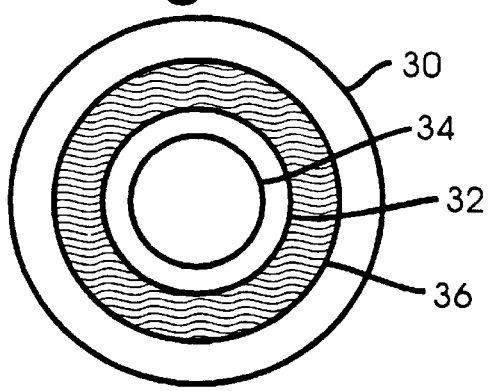
FIG. 5 is a cross sectional view of the catheter-electrode taken along line 5—5 of FIG. 6.

The distal end of catheter 22 terminates in a cylindrical hollow tube 22A having a distal end 25 implanted into a portion of the basal ganglia of the brain by conventional stereotactic surgical techniques. End 25 is provided with microporous portions 27–29 in the preferred embodiment (FIG. 6); however, multiple holes or slits within portions 27–29 could also be used. Additional details about portions 27–29 may be obtained from pending U.S. application Ser. No. 08/430,960 entitled "Intraparenchymal Infusion Catheter System," filed Apr. 28, 1995, in the name of Dennis Elsberry et al. and assigned to the same assignee as the present application. Referring to FIG. 5, tube 22A includes an outer cylindrical insulating jacket 30 and an inner cylindrical insulating jacket 32 that defines a cylindrical catheter lumen 34. A multifilar coil, strands of wire or flexible printed circuit 36 is embedded in tube 22A as shown.

Tube 22A is surgically implanted through a hole in the skull 123 and catheter 22 is implanted between the skull and the scalp 125 as shown in FIG. 1. A stylet may be placed into the center of tube 22A to give it stiffness when introducing the tube into the brain or other neural tissue. After the stylet is removed, center lumen 34 constitutes a catheter which can be used to infuse an agent, including a drug. Catheter 22 is joined to implanted device 10 in the manner shown.

Device 10 is implanted in a human body in a subclavicular, subcutaneous pocket. Alternatively, device 10 may be implanted in the abdomen.

Catheter 22 may be divided into twin tubes 22A and 22B (not shown) that are implanted into the brain bilaterally (not shown). Alternatively, tube 22B may be supplied with drugs from a separate catheter and pump.

Referring again to FIG. 1, a system or device 16 made in accordance with the preferred embodiment also may be implanted below the skin of a patient. Device 16 may take the form of a modified signal generator Model 7424 manufactured by Medtronic, Inc. under the trademark Itrel II which is incorporated by reference.

The distal end of tube 22A terminates in stimulation electrodes 38 and 40 (FIG. 6) that can stimulate neurons N1–N3. Each of electrodes 38 and 40 is individually connected to device 16 through a conductor in wire 36 (FIG. 5). The wires exit catheter 22 to form a cable 42 which is joined to implanted device 16 in the manner shown in FIG. 1. While the preferred embodiment shows two electrodes on tube 22A (FIG. 6), some applications may require a greater number.

Referring to FIG. 1, device 16 is implanted in a human body also in a subclavicular, subcutaneous pocket. Alternatively, device 16 may be implanted elsewhere, such as in the abdomen.

A sensor 130 is implanted into a portion of a patient's body suitable for detecting a condition resulting from the onset of a seizure, including a seizure itself The sensor includes a tube 50 that carries recording electrodes 52 and 53. Sensor 130 is adapted to sense an attribute of the body that changes in advance of or during a seizure. Sensor 130 may be located on a separate lead as shown in FIG. 1 or it may be located on tube 22A.

Sensor 130 may take the form of a device capable of detecting nerve cell or axon activity that is related to the pathways at the cause of a seizure symptom, or that indicates sensations which are elicited by the onset of a seizure. Such a sensor may be located deep in the brain as show in FIG. 1. For such detecting, sensor 130 may take the form of an electrode inserted into the thalamus, internal capsule, hippocampus, cortex or basal ganglia of the brain. Alternatively, the electrode may be inserted into the seizure focus or part of the central nervous system where seizures begin. Signals that are received by the sensor may by amplified before transmission to circuitry contained within device 10 or device 16. Brain EEG recorded above the cortical surface also may be detected by sensor 130.

Yet another form of sensor 130 would include a device capable of detecting nerve compound action potentials (e.g., either sensory afferent information from muscle or skin receptors or efferent motor potentials controlling a muscle of interest).

Sensor 130 may take the form of a transducer consisting of an electrode with an ion selective coating applied which is capable of directly transducing the amount of a particular transmitter substance or its breakdown by-products found in the interstitial space of a region of the brain such as the hippocampus or thalamus. The level of the interstitial transmitter substance is an indicator of the relative activity of the brain region and the onset of a seizure. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters*, 120 (1990) 249–252.

Sensor 130 may sense three-dimensional or two-dimensional motion characteristic of seizure activity, such as by an accelerometer. One such sensor suitable for use with the present invention is described in U.S. Pat. No. 5,293,879 (Vonk et al.). Another suitable accelerometer is found in pacemakers manufactured by Medtronic, Inc. and described in U.S. patent application Ser. No. 08/399072 entitled "Package Integrated Accelerometer", filed Mar. 8, 1995, in the names of James Sikorski and Larry R. Larson. Sensor 130 also may be placed in device 10 in order to detect abnormal movement resulting from the motion disorder being treated.

Sensor 130 also may be capable of detecting gravity direction or motion relative to some object (e.g., a magnet) either implanted or fixed nearby. Sensor 130 need not be implanted in the brain. Sensor 130 also may take the form of a device capable of detecting force in muscles or at joints, or pressure.

Sensor 130 may detect muscle EMG in one, two or more muscles, or in reciprocal muscles at one joint. For such detection, sensor 130 may take the form of a lead with one or more recording electrodes inserted into the muscle of interest.

For certain types of patients, sensor 130 may take the form of a device detecting the posture of the patient, such as the device shown in U.S. Pat. No. 5,031,618 (Mullett).

Sensor 130 may detect physiological parameters such as heart rate or respiration rate. Sensor 130 may be physically located outside of the body and communicate with the implanted portion through telemetry.

Figure 2:
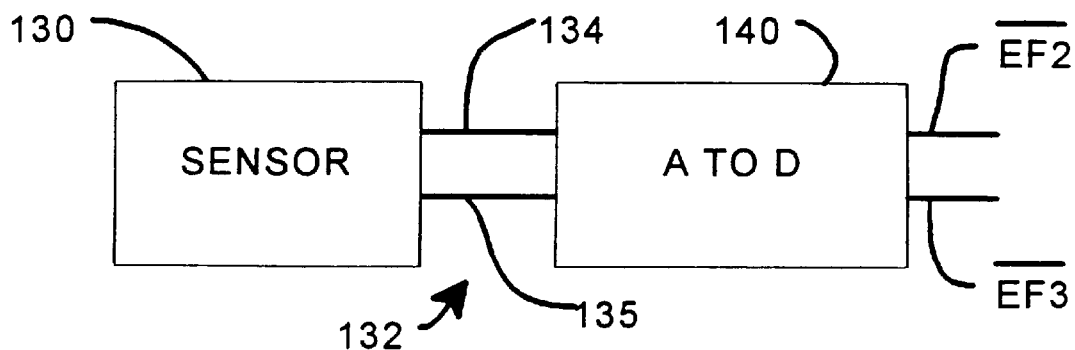
FIG. 2 is a schematic block diagram of a sensor and analog to digital converter circuit used in the preferred embodiment of the invention.

Referring to FIG. 2, the outputs of electrodes 52 and 53 of sensor 130 are coupled by a cable 132 comprising conductors 134 and 135 to the input of analog to digital converter 140. Alternatively, the output of an external feedback sensor would communicate with the implanted pulse generator through a telemetry downlink. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A would be disconnected.

The present invention may be implemented by providing seven different drug dosages from 0 dosage to a 1.0 ml dosage with 0.1 ml increments between choices. The time interval between dosages can be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B) of the '147 Patent. The appropriate drug dosage and interval is selected by a computer algorithm that reads the output of converter 140 and makes the appropriate selection.

Figure 3:
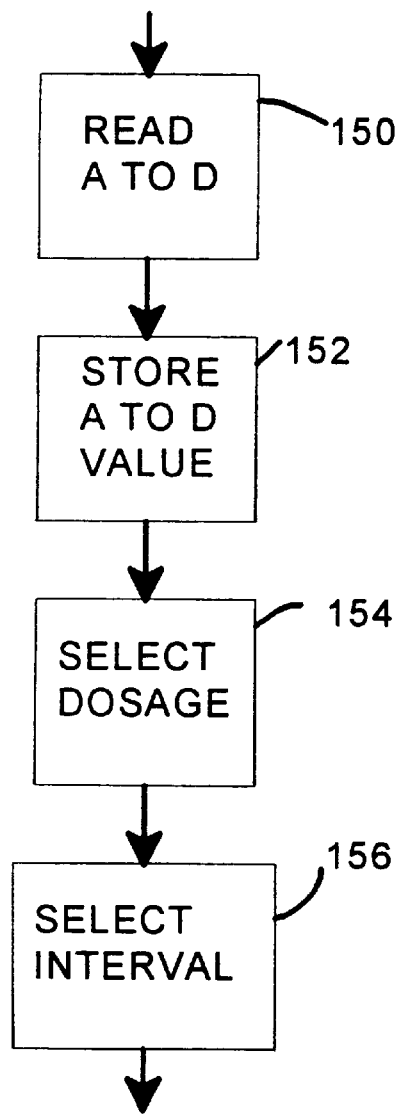
FIG. 3 is a flow chart illustrating a preferred form of a microprocessor program for utilizing the sensor to control drug dosage administered to the brain.

One exemplary computer algorithm is shown in FIG. 3. Microprocessor 100 included within device 10 reads converter 140 in step 150, and stores one or more values in RAM 102a in step 152. One of seven dosages is selected in step 154, and an appropriate time interval is selected in step 156. The selected dosage and interval of a drug is then delivered through catheter 22 and tube 22A to the basal ganglia of the brain as described in the '147 Patent.

For some types of seizure disorders, a microprocessor and analog to digital converter will not be necessary. The output from sensor 130 can be filtered by an appropriate electronic filter in order to provide a control signal for a pump of the type shown in the '147 Patent.

The type of drugs administered by device 10 into the brain depend on the specific location at which distal end 25 of tube 22A is surgically implanted. The appropriate drugs for use in connection with the portion of the basal ganglia or thalamus in which tube 22A terminates, together with the effect of the drug on that portion of the brain is provided in the following Table I:

TABLE I

| EFFECT | PORTION OF BRAIN | DRUG |
| --- | --- | --- |
| DESYNCHRONIZE NEURONAL ACTIVITY | SEIZURE FOCUS | GABA agonist/uptake inhibitor, Glutamate antagonist, Anesthetic |
| INCREASE INHIBITION | ANTERIOR THALAMUS | GABA agonist/uptake inhibitor |
| DECREASE EXCITATION | ANTERIOR THALAMUS | Glutamate antagonist |
| INCREASE EXCITATION | VL THALAMUS | Glutamate agonist/uptake inhibitor |
| DECREASE INHIBITION | VL THALAMUS | GABA antagonist |

TABLE I-continued

| EFFECT | PORTION OF BRAIN | DRUG |
|---|---|---|
| INCREASE INHIBITION | GPi/SNr | GABA agonist/uptake inhibitor |
| DECREASE EXCITATION | GPi/SNr | Glutamate antagonist |
| INCREASE INHIBITION | STN | GABA agonist/uptake inhibitor |
| DECREASE EXCITATION | STN | Glutamate antagonist |
| INCREASE EXCITATION | GPe | Glutamate agonist/uptake inhibitor |
| DECREASE INHIBITION | GPe | GABA antagonist |
| INCREASE DOPAMINE | NEOSTRIATUM | Dopamine agonist/uptake inhibitor |

In the foregoing Table I, VL Thalamus means ventrolateral thalamus; GPi means internal segment of globus pallidus; SNr means substantia nigra, STN means subthalamic nucleus; neostriatum means the combination of the caudate nucleus and the putamen; and GPe means external segment of globus pallidus.

Typical stereotaxic coordinates for the portions of a normal brain described in Table I are identified in the following Table II:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| Anterior Thalamus | 0.2 to 1.2 | 0.2 TO 1.3 | 0.5 TO −0.5 |
| VL Thalamus | 0.7 to 1.8 | 1.5 to −0.2 | 0.0 to −1.0 |
| GPi | 0.5 to 2.0 | 0.5 to −0.7 | 0.7 to 2.0 |
| SN | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissure with negative being ventral to; all dimensions are in centimeters.

Exemplary ranges of dosages and drug concentrations for the drugs identified in Table I are provided in the following Table III:

TABLE III

| DRUG CLASS | SPECIFIC DRUG | DOSING RANGE |
|---|---|---|
| Glutamate Agonist | D-Cycloserine | 1–10 muM |
| | L-AP4 | 1–10 muM |
| | Carboxyphenylglycine | 10–500 muM |
| | L-glutamic acid | 1–100 muM |
| | cis-Piperidine-2,3-dicarboxylic acid | 1–10 muM |
| | (+/−)-trans-ACPD | 1–10 muM |
| | L-AP4 | 1–10 muM |

TABLE III-continued

| DRUG CLASS | SPECIFIC DRUG | DOSING RANGE |
|---|---|---|
| Glutamate Antagonists | MK801(dizocilpine) | 1–20 muM |
| | ketamine Hcl | 5–50 muM |
| | AP-3 | 1–10 muM |
| | Dextromethorphan | 1–100 muM |
| | MCPD | 0.02–10 muM |
| | dextrorphan tartrate | 1–100 muM |
| | CNQX | 1–100 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphine Hcl | 5–20 muM |
| | spiperone Hcl | 0.1–10 muM |
| | haloperidol | 10–100 muM |
| | (−) Sulpiride | 0.05–1 muM |
| Dopamine Agonist | methanesulfonate | 1–10 muM |
| Dopamine Agonist (cont.) | (−) apomorphine pergolide | 10–30 muM |
| Anesthetic | Lidocaine hydrochloride | 5–20 muM |

In the Preceding Table, MuM Means Micromolar

Alternatively, these agents might be infused into the lateral ventricle or third ventricle of the brain or just beneath the dura above the cortex or in the intrathecal space. In this instance the drug would diffuse to the appropriate site of action.

A drug can be delivered essentially continuously (within the constraints of the particular delivery device being used) or it may be delivered during intermittent intervals coordinated to reflect the half-life of the particular agent being infused or circadian rhythms. As an example, seizures may normally increase at night when the person is sleeping so the drug delivery rates might be increased to coincide with the hours between 10 p.m. and 7 a.m.

Microprocessor 100 within device 10 can be programmed so that a controlled amount of drug can be delivered to the specific brain sites described in Table I. Alternatively, sensor 130 can be used with a closed loop feedback system in order to automatically determine the level of drug delivery necessary to alleviate neural symptoms as described in connection with FIG. 3.

Figure 4:
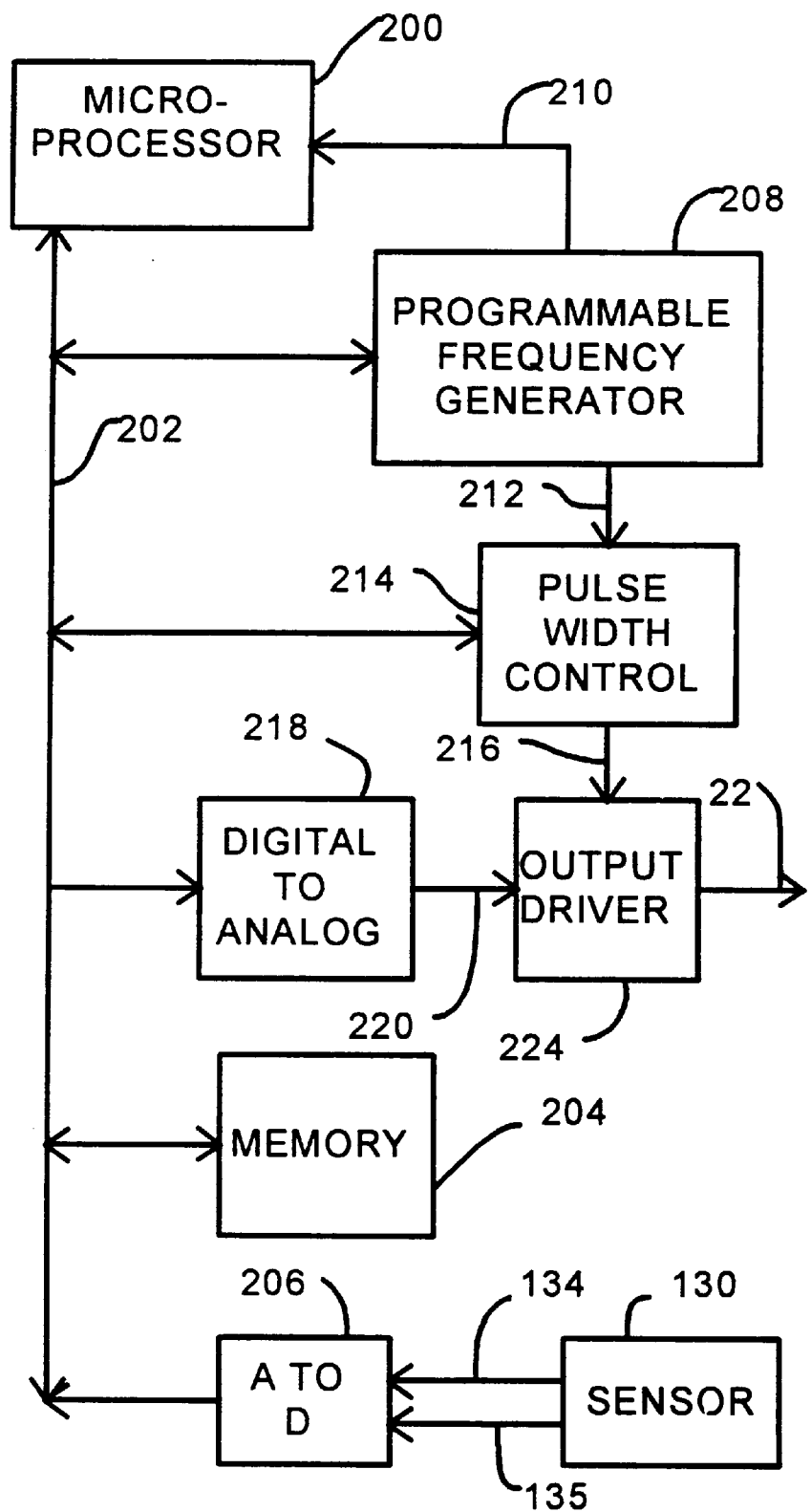
FIG. 4 is a schematic block diagram of a microprocessor and related circuitry for utilizing the sensor to control stimulation administered to the brain.

The applicants have discovered that the efficacy of treatment may be enhanced if the neural tissue is stimulated while drugs are being administered as described above. The stimulation can be achieved by a modified form of the ITREL II signal generator implemented as device 16 (FIG. 1) which is described in FIG. 4. The output of sensor 130 is coupled by cable 132, comprising conductors 134 and 135, to the input of an analog to digital converter 206. Alternatively, the output of an external sensor would communicate with the implanted pulse generator through a telemetry downlink. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 22 and lead 22A to the basal ganglia, thalamus or other region of the brain.

Microprocessor 200 executes an algorithm (not shown) in order to provide stimulation with closed loop feedback control. At the time the stimulation device 16 is implanted, the clinician programs certain key parameters into the memory of the implanted device via telemetry. These parameters may be updated subsequently as needed. Alternatively, the clinician may elect to use default values. The clinician must program the range of values for pulse width, amplitude and frequency which device 10 may use to optimize the therapy.

The algorithm for selecting parameters is different depending on whether the clinician has chosen to block the neural activity at the stimulation target or facilitate the neural activity. If the neuronal activity is to be blocked, device 16 will be programmed with a frequency in the range 50 to 2500 Hz. If the neuronal activity is to be facilitated, the stimulus frequency is chosen in the range of 2 to 100 Hz.

The stimulation may be applied continuously to prophylactically prevent the onset of seizures or it may turn on in response to a signal on sensor 130 indicating the beginning of a seizure. Stimulus parameters can be adjusted by the computer algorithm within a range specified by the clinician in an attempt to optimize the seizure suppression.

Electrical stimulation of neural tissue may be implemented by providing pulses to electrodes 38 and 40 (FIG. 6) having amplitudes of 0.1 to 20 volts, pulse widths varying from 0.02 to 1.5 milliseconds, and repetition rates varying from 2 to 2500 Hz. The appropriate stimulation pulses are generated by device 16 based on the computer algorithm and parameters set by the clinician.

For some types of seizure disorders, a microprocessor and analog to digital converter will not be necessary. The output from sensor 130 can be filtered by an appropriate electronic filter in order to provide a control signal for device 16.

The type of stimulation administered by device 16 to the brain depends on the specific location at which the electrodes 38 and 40 of tube 22A are surgically implanted. The appropriate stimulation for the portion of the basal ganglia or thalamus in which tube 22A terminates, together with the effect of the stimulation on that portion of the brain for seizure disorders is provided in the following Table IV:

TABLE IV

| EFFECT | STIMULUS TYPE | LOCATION |
|---|---|---|
| DESYNCHRONIZE SEIZURE FOCUS | HIGH FREQUENCY | SEIZURE FOCUS |
| INCREASE EXCITATION OF VL THALAMUS | LOW FREQ. STIMULATION | VL THALAMUS |
| DECREASE INHIBITION OF VL THALAMUS | HIGH FREQ. BLOCKING STIMULATION | GPi/SNr |
| DECREASE EXCITATION OF ANTERIOR THALAMUS | HIGH FREQUENCY | ANTERIOR THALAMIC NUCLEUS |
| INCREASE INHIBITION OF GPi/SN | LOW FREQ. STIMULATION | Striatopallidal fiber pathway |
| INCREASE INHIBITION OF GPi/SN | LOW FREQ. STIMULATION | Neostriatum |
| DECREASE EXCITATION OF GPi/SN | HIGH FREQ. BLOCKING STIMULATION | GPi/SNr |
| INCREASE INHIBITION OF STN | LOW FREQ. STIMULATION | GPe to STN fiber pathway |
| INCREASE INHIBITION OF STN | LOW FREQ. STIMULATION | GPe |
| DECREASE EXCITATION OF STN | HIGH FREQ. BLOCKING STIMULATION | STN |
| INCREASE EXCITATION OF GPe | LOW FREQ. ACTIVATING STIMULATION | GPe |
| DECREASE INHIBITION OF GPe | HIGH FREQ. BLOCKING STIMULATION | Neostriatum |
| INCREASE INHIBITION OF GPi/SN | LOW FREQ. ACTIVATING STIMULATION | STRIATOPALLIDAL FIBER PATHWAYS |

In the foregoing Table IV, VL Thalamus means ventrolateral thalamus; GPi means internal segment of globus pallidus; SN means substantia nigra, STN means subthalamic nucleus; LT means the Lenticulo-thalamic fiber pathway; neostriatum means the combination of the caudate nucleus and the putamen; and GPe means external segment of globus pallidus.

Coordinates for the portions of the brain described in Table IV are the same as described in connection with Table II.

A microprocessor or custom integrated circuit within device 16 can be programmed so that the desired stimulation can be delivered to the specific brain sites described in Table IV. Alternatively, sensor 130 can be used with a closed loop feedback system in order to automatically determine the type of stimulation necessary to alleviate seizure symptoms oased on the above-described treatment regimen.

Figure 7A:
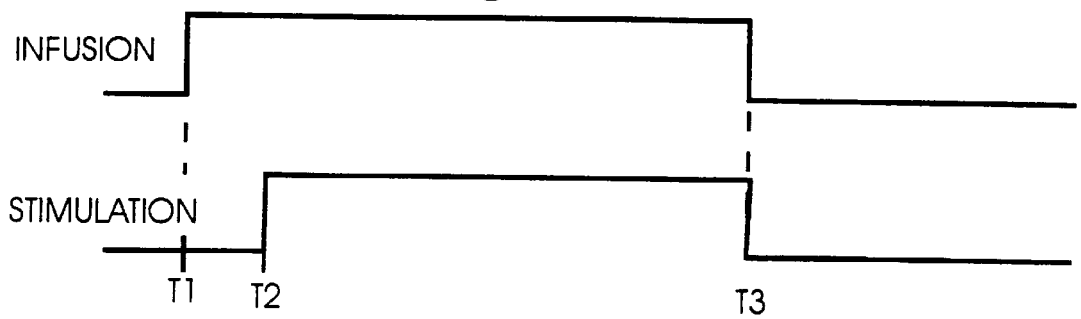
FIGS. 7A–7C are timing diagrams showing the relationship between the administration of drugs and electrical stimulation to neural tissue.
Figure 7B:
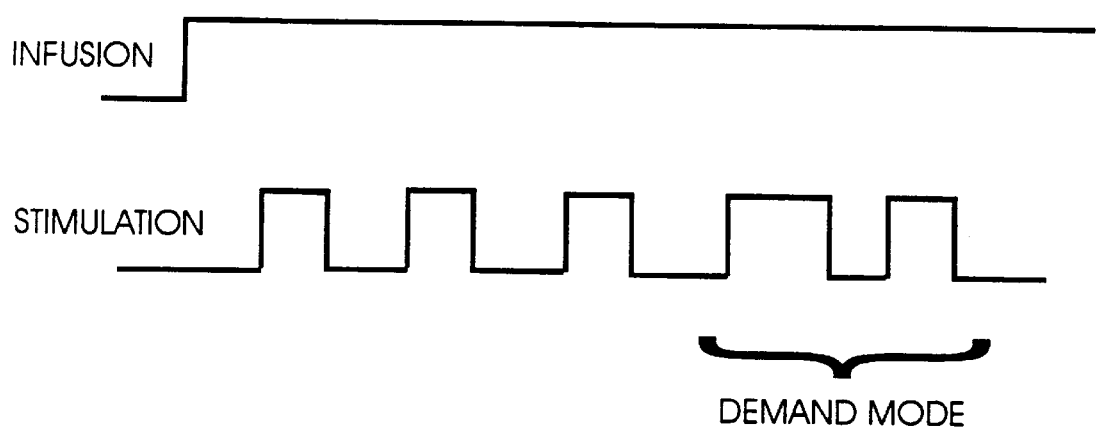
Figure 7C:
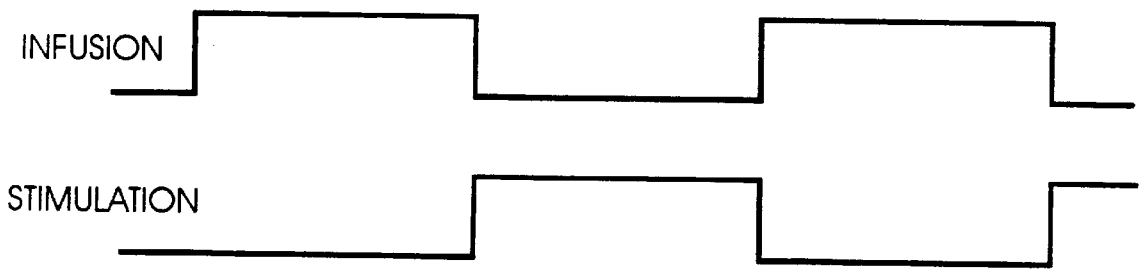

FIGS. 7A–7C illustrate various times at which infusion and stimulation can be applied by tube 22A. For example, referring to FIG. 7A, following recognition of neural activity suggesting the onset of a seizure, infusion alone can be applied from time T1 to T2. If the infusion is adequate to suppress the neural activity, thereby preventing the onset of the seizure, the infusion would stop after some time has elapsed or after a change in the signal detected by sensor 130. If, on the other hand, the neural activity detected by sensor 130 indicates potential seizure activity is not being suppressed, then infusion and stimulation can be both be applied from time T2 to T3 in an effort to suppress the seizure. Infusion and stimulation would be terminated after some time has elapsed or after an appropriate change of the signal on sensor 130. While stimulation is superposed on the background of infusion in this embodiment, applying infusion on a background of stimulation is also possible and may be equally or more effective for some seizure types.

Referring to FIG. 7B, the stimulation might be applied periodically during the period of infusion either routinely or in response to sensor or patient generated demand. A continuous tonic infusion of a pharmaceutical agent (or stimulation) uncoupled from any sensor would provide general seizure suppression while coupling the stimulation (or infusion) to the sensor signal would provide additional therapy in response to a "break through" seizure.

Referring to FIG. 7C, the infusion of an agent to activate a neuronal population might be alternated with application of electrical stimulation of that same population. Alternating the infusion and stimulation therapies may provide added benefit to continuously applying only one form of therapy.

By using the foregoing techniques for drug infusion and electrical stimulation, neural disorders, including epilepsy, can be controlled with a degree of accuracy previously unattainable. Those skilled in that art will recognize that the preferred embodiments may be altered or amended without departing from the true spirit and scope of the invention, as defined in the accompanying claims.

We claim:

1. A method of using at least one drug to treat epilepsy by means of an implantable pump and a catheter having a proximal end coupled to said pump and a discharge portion for infusing therapeutic dosages of said at least one drug, said method comprising the steps of:

surgically implanting said catheter in the brain so that said discharge portion lies adjacent a predetermined infusion site in the brain, wherein said predetermined infusion site is selected from the group consisting of the seizure focus, anterior thalamus, ventrolateral thalamus (Thal), internal segment of globus pallidus (GPi), substantia nigra pars reticulata (SNr), subthalamic nucleus (STN), external segment of globus pallidus (GPe), and neostriatum; and operating said pump to discharge a predetermined dosage of said at least one drug through said discharge portion of said catheter into said infusion site, whereby a neurological disorder is treated.

2. A method, as claimed in claim 1, wherein said at least one drug increases excitation or deceases inhibition of at least one of said ventrolateral thalamus (Thal) and external segment of globus pallidus (GPe).

3. A method, as claimed in claim 1, wherein said at least one drug increases inhibition or decreases excitation of at least one of said anterior thalamus, internal segment of globus pallidus (GPi), substantia nigra pars reticulata (SNr) and subthalamic nucleus (STN).

4. A method, as claimed in claim 1, wherein said at least one drug is selected from the group consisting of a glutamate antagonist, a glutamate agonist, a γ-aminobutyric acid (GABA) antagonist, a γ-aminobutyric acid (GABA) agonist, a dopamine (DA) agonist and an anesthetic.

5. A method, as claimed in claim 1, and further comprising the steps of:

generating a sensor signal in response to a condition resulting from the onset of a seizure; and altering said operation of said pump in response to said sensor signal for changing said predetermined dosage.

6. A method of treating a neurological disorder producing a condition resulting from the onset of a seizure, comprising:

implanting a signal generator in a body;

implanting at least one electrode in at least one predetermined site in a brain of said body;

coupling said at least one electrode to said signal generator;

generating a sensor signal responsive to said condition resulting from an onset of a seizure;

generating stimulation pulses with said signal generator; and regulating at least one characteristic of said stimulation pulses in response to said sensor signal, whereby said neurological disorder is treated.

7. A method, as claimed in claim 6, wherein said predetermined site is selected from the group consisting of the subthalamic nucleus (STN), external segment of globus pallidus (GPe), and substantia nigra pars reticulata (SNr).

8. A method, as claimed in claim 6, wherein said step of generating a sensor signal comprises the step of detecting neuronal activity.

9. A method, as claimed in claim 6, wherein said step of regulating comprises the step of executing a control algorithm.

10. A method, as claimed in claim 6, wherein said at least one characteristic includes a pulse amplitude.

11. A method, as claimed in claim 6, wherein said at least one characteristic includes a pulse frequency.

12. A method, as claimed in claim 6, wherein said at least one characteristic includes a pulse width.

13. A method, as claimed in claim 6, wherein said at least one characteristic includes a pulse amplitude, a pulse frequency, and a pulse width.

14. A method, as claimed in claim 9, wherein said at least one characteristic includes pulse amplitude, a pulse frequency, and a pulse width.

15. A system for using one or more drugs to treat a neurological disorder producing a condition resulting from the onset of a seizure comprising in combination:

an implantable pump;

a catheter having a proximal end coupled to said pump and a discharge portion adapted to infuse a predetermined dosage of said one or more drugs into a predetermined infusion site in a brain;

a sensor for generating a sensor signal responsive to said condition resulting from the onset of a seizure; and control means responsive to said sensor signal for determining the onset of a seizure and for regulating said dosage, whereby said neurological disorder is treated.

16. A system, as claimed in claim 15, wherein said sensor comprises means for detecting neuronal activity.

17. A system, as claimed in claim 15, wherein said control means comprises a microprocessor.

18. A system, as claimed in claim 15, wherein said control means comprises an electrical filter.

19. A system, as claimed in claim 15, and further comprising:

a signal generator for generating stimulation pulses; and one or more electrodes responsive to said stimulation pulses for electrically stimulating said predetermined infusion site, whereby said neurological disorder is treated by drug infusion and electrical stimulation, wherein said control means is responsive to said sensor signal for regulating said dosage and said stimulation pulses.

20. A system for using at least one drug to treat a neurological disorder producing a condition resulting from the onset of a seizure comprising in combination:

an implantable pump;

a signal generator for generating stimulation pulses;

a combined catheter-electrode having a proximal end coupled to said pump and said signal generator and a distal end adapted to infuse a predetermined dosage of at least one drug into a predetermined infusion site in a brain, said distal end also having at least one electrode responsive to said stimulation pulses for electrically stimulating said predetermined infusion site;

a sensor for generating a sensor signal responsive to said condition resulting from the onset of a seizure and having means for detecting neuronal activity; and control means responsive to said sensor signal for regulating said dosage and stimulation pulses, whereby said neurological disorder is treated.

21. A method of using at least one drug to treat epilepsy by means of an implantable pump and a catheter having a proximal end coupled to said pump and a discharge portion for infusing therapeutic dosages of said at least one drug, said method comprising the steps of:

surgically implanting said catheter so that said discharge portion lies adjacent a predetermined infusion site above the cortex of the brain; and operating said pump to discharge a predetermined dosage of said at least one drug through said discharge portion of said catheter into said infusion site, whereby a neurological disorder is treated.

22. A method, as claimed in claim 21, wherein said at least one drug is selected from the group consisting of a glutamate antagonist, a glutamate agonist, a γ-aminobutyric acid (GABA) antagonist, a γ-aminobutyric acid (GABA) agonist, a dopamine (DA) agonist and an anesthetic.

23. A method, as claimed in claim 21, and further comprising the steps of:

generating a sensor signal in response to a condition resulting from the onset of a seizure; and altering said operation of said pump in response to said sensor signal for changing said predetermined dosage.

* * * * *